US012704856B1

(12) United States Patent
Hoo et al.

(10) Patent No.: US 12,704,856 B1
(45) Date of Patent: Aug. 11, 2026

(54) SECURE HIGH-PRECISION DELIVERY SYSTEM AND METHOD

(71) Applicant: UIPCO, LLC, San Antonio, TX (US)

(72) Inventors: Soon Fatt Hoo, Tahlequah, OK (US); Seth E. Ethington, McKinney, TX (US); Eric Leroy, Flower Mound, TX (US); Qian Zhao, Dallas, TX (US); Shawnta Nicole Swindell, McLean, VA (US); Navaid Hussain, Dallas, TX (US); Jessica De los Rios, San Antonio, TX (US); Jake Hsiao, Allen, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 179 days.

(21) Appl. No.: 18/427,057

(22) Filed: Jan. 30, 2024

Related U.S. Application Data

(60) Provisional application No. 63/482,130, filed on Jan. 30, 2023.

(51) Int. Cl.
*G05D 1/667* (2024.01)
*A61L 2/10* (2006.01)
(Continued)

(52) U.S. Cl.
CPC ................ *G05D 1/667* (2024.01); *A61L 2/10* (2013.01); *A61L 2/18* (2013.01); *B64D 1/02* (2013.01);
(Continued)

(58) Field of Classification Search
CPC .... G05D 1/667; G05D 1/665; G05D 2111/30; G05D 2109/20; G05D 2105/20;
(Continued)

(56) References Cited

U.S. PATENT DOCUMENTS 6,054,950 A * 4/2000 Fontana .................... G01S 5/06 342/464
8,958,928 B2 * 2/2015 Seydoux ............. G06F 3/04817 345/173
(Continued)

FOREIGN PATENT DOCUMENTS

JP 2022113184 A 8/2022

OTHER PUBLICATIONS

Victor R. F. Miranda et al., Autonomous Navigation System for a Delivery Drone, Jun. 16, 2021, arXiv, pp. 1-13 (pdf).*
(Continued)

*Primary Examiner* — Manglesh M Patel
(74) *Attorney, Agent, or Firm* — Plumsea Law Group, LLC

(57) ABSTRACT

A system and method for automated guidance of a drone or delivery person via a local (on-site) UWB device for high-precision delivery of items is provided. The drone or delivery person arrives at a standard address such as a house, and comes into range of the UWB device. The UWB localization signal transmitted by the UWB device is received by the delivery agent and used to generate navigation guidance to a specific target destination for package delivery. In some embodiments, a smart container system including a UWB device may also be provided to improve security and appropriate ambient conditions for the package.

19 Claims, 11 Drawing Sheets

(51) Int. Cl.

| | |
|---|---|
| ***A61L 2/18*** | (2006.01) |
| ***B64D 1/02*** | (2006.01) |
| ***B65D 81/18*** | (2006.01) |
| ***G05D 1/656*** | (2024.01) |
| ***G05D 105/20*** | (2024.01) |
| ***G05D 109/20*** | (2024.01) |
| ***G06Q 10/0832*** | (2023.01) |
| ***G06Q 10/0833*** | (2023.01) |
| ***H04W 4/40*** | (2018.01) |
| ***H04W 4/80*** | (2018.01) |
| *G05D 111/30* | (2024.01) |

(52) U.S. Cl.

CPC ......... *G05D 1/665* (2024.01); *G06Q 10/0832* (2013.01); *G06Q 10/0833* (2013.01); *H04W 4/40* (2018.02); *H04W 4/80* (2018.02); *A61L 2202/122* (2013.01); *G05D 2105/20* (2024.01); *G05D 2109/20* (2024.01); *G05D 2111/30* (2024.01)

(58) Field of Classification Search

CPC ...... G05D 1/00–12; H04W 4/80; H04W 4/40; A61L 2/10; A61L 2/18; A61L 2202/122; B64D 1/02; G06Q 10/0832; G06Q 10/0833; B65D 81/18

USPC .............................................................. 701/3

See application file for complete search history.

(56) References Cited

U.S. PATENT DOCUMENTS

| | | | | |
|---|---|---|---|---|
| 9,573,684 | B2 * | 2/2017 | Kimchi | B64U 50/19 |
| 10,692,038 | B2 | 6/2020 | Stuckman | |
| 10,726,381 | B2 * | 7/2020 | Cooper | G08G 5/57 |
| 10,775,792 | B2 | 9/2020 | Cooper | |
| 10,839,336 | B2 | 11/2020 | Greiner | |
| 11,393,346 | B1 | 7/2022 | Ogun | |
| 2009/0120653 | A1 * | 5/2009 | Thomas | A62C 5/02 169/61 |
| 2014/0032034 | A1 * | 1/2014 | Raptopoulos | G08G 5/55 701/25 |
| 2015/0158599 | A1 * | 6/2015 | Sisko | B64F 1/20 244/114 R |
| 2016/0302044 | A1 * | 10/2016 | Bottazzi | H04W 4/30 |
| 2017/0147975 | A1 * | 5/2017 | Natarajan | G06Q 10/0832 |
| 2017/0203857 | A1 * | 7/2017 | O'Toole | A47G 29/141 |
| 2017/0337826 | A1 | 11/2017 | Moran | |
| 2018/0244404 | A1 | 8/2018 | Park | |
| 2018/0352988 | A1 * | 12/2018 | Ortiz | B64F 1/32 |
| 2019/0130342 | A1 | 5/2019 | Maheshwari | |
| 2019/0227576 | A1 * | 7/2019 | High | G05D 1/0094 |
| 2019/0369641 | A1 * | 12/2019 | Gillett | G05D 1/0088 |
| 2020/0050408 | A1 * | 2/2020 | Wushour | G06F 3/1204 |
| 2020/0116856 | A1 * | 4/2020 | Roberts | G01S 13/46 |
| 2020/0288895 | A1 * | 9/2020 | Bennet | H04W 12/08 |
| 2020/0398999 | A1 * | 12/2020 | Ortiz | G07C 9/00563 |
| 2020/0408028 | A1 * | 12/2020 | Schmider | A47B 87/008 |
| 2021/0045564 | A1 | 2/2021 | Duckers | |
| 2021/0103023 | A1 * | 4/2021 | Al-kadi | G01S 5/02216 |
| 2022/0044198 | A1 * | 2/2022 | Meister | G06Q 10/0833 |
| 2022/0146618 | A1 * | 5/2022 | Wu | G01S 5/021 |
| 2022/0207472 | A1 * | 6/2022 | Hashisho | G06V 20/13 |
| 2023/0213664 | A1 * | 7/2023 | Kulkarni | G01C 21/3807 342/357.31 |
| 2023/0363562 | A1 * | 11/2023 | O'Toole | A47G 29/16 |
| 2024/0303318 | A1 * | 9/2024 | Wright | G06Q 10/083 |

OTHER PUBLICATIONS

Sangmin Lee et al., Drone Positioning System Using UWB sensing and Out-of-Band Control, Mar. 15, 2022, IEEE Sensors Council, pp. 5329-5343.*

Wang Shule et al., UWB-Based Localization for Multi-UAV Systems and Collaborative Heterogeneous Multi-Robot Systems, 2020, Elsevier, pp. 657-364.*

Machine Translation JP 2022113184 (Year: 2022).

Non-Final Office Action mailed Mar. 16, 2023 for U.S. Appl. No. 17/513,373.

Final Office Action mailed Oct. 10, 2023 for U.S. Appl. No. 17/513,373.

Non-Final Office Action mailed May 2, 2024 for U.S. Appl. No. 17/513,373.

* cited by examiner

SECURE HIGH-PRECISION DELIVERY SYSTEM AND METHOD

CROSS-REFERENCE TO RELATED APPLICATION

This application claims the benefit of U.S. Provisional Patent Application Ser. No. 63/482,130 filed on Jan. 30, 2023 and titled "Secure High-Precision Delivery System and Method", the disclosure of which is incorporated by reference herein in its entirety.

TECHNICAL FIELD

The present disclosure generally relates to navigation control techniques, and in particular to a system and method for more precisely guiding an unmanned vehicle (UV) to a specific target on a property site once the UV is in proximity of the site.

BACKGROUND

Drones, or unmanned vehicles (UVs), in particular unmanned aerial vehicles (UAVs), show high potential for parcel delivery. Drone delivery may be faster, less expensive, and more eco-friendly than traditional delivery modes such as trucks. Although drones are not yet in regular commercial use, many companies have initiated pilot tests, with the expectation that the mechanism will become common in the future.

However, existing approaches either focus on rural areas or rely on centralized drop-off locations from where the last mile delivery is performed. Conventional drone delivery systems are designed for delivery of a package to a farm or an estate, with no other house in sight. In reality, a growing number of people in the world live in dense urban areas, and in apartments or condominiums. According to World Bank data, urban living is the norm already today, and its share is growing steadily. The urban "last mile problem" is a barrier to wider use of drone delivery systems. For example, in a multi-story house environment, the issue does not end with finding the right building—as a next step the drone needs to find the right apartment. Then, the drone must drop the packet at the right location, usually a balcony with limited space for maneuvering. While doing all this, the drone needs to circumnavigate any obstructions. Current drone navigation is ill-equipped to perform these tasks.

There is a need in the art for a system and method that addresses the shortcomings discussed above.

SUMMARY

In one aspect, a method for high-precision delivery of items using ultra-wide band (UWB), such as guiding an unmanned aerial vehicle (UAV) to a micro-destination, is disclosed. A first step includes causing, via an onboard computing system of an unmanned vehicle (UV), the UV to travel to an initial position near a first property, the initial position being in range of a first UWB localization signal generated from a first UWB device on the first property. A second step includes determining, at the onboard computing system, a first position of the first UWB device relative to the UV based on the first UWB localization signal. In addition, a third step includes causing, via the onboard computing system, the UV to travel from the initial position to a first micro-destination associated with the first position.

In another aspect, a method of secure delivery of items using a smart container system is disclosed. The method includes a first step of transmitting, from a first ultra-wide band (UWB) device included in a first smart container disposed at a first property, a first UWB localization signal to a first delivery computing device, and a second step of receiving, at an onboard computing device of the first smart container and from the first delivery computing device, a first request signal. The method also includes a third step of verifying, at the first smart container, that the first request signal represents a valid request to access an interior chamber of the first smart container, and a fourth step of opening, at the first smart container and in response to the verification, a first door to provide access to the interior chamber. A fifth step includes receiving, from a position directly above the interior chamber, a package, and a sixth step includes detecting, via one or more sensors included in a base of the first smart container, a presence of the package. In addition, a seventh step includes closing, in response to detecting the presence of the package, the first door, thereby resealing the first smart container.

In another aspect, a system for high-precision delivery of items using ultra-wide band (UWB) includes a processor and machine-readable media including instructions which, when executed by the processor, cause the processor to cause, via an onboard computing system of an unmanned vehicle (UV), the UV to travel to an initial position near a first property, the initial position being in range of a first UWB localization signal generated from a first UWB device on the first property. The instructions further cause the processor to determine, at the onboard computing system, a first position of the first UWB device relative to the UV based on the first UWB localization signal, and to cause, via the onboard computing system, the UV to travel from the initial position to a first micro-destination associated with the first position.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF THE EMBODIMENTS

Figure 1:
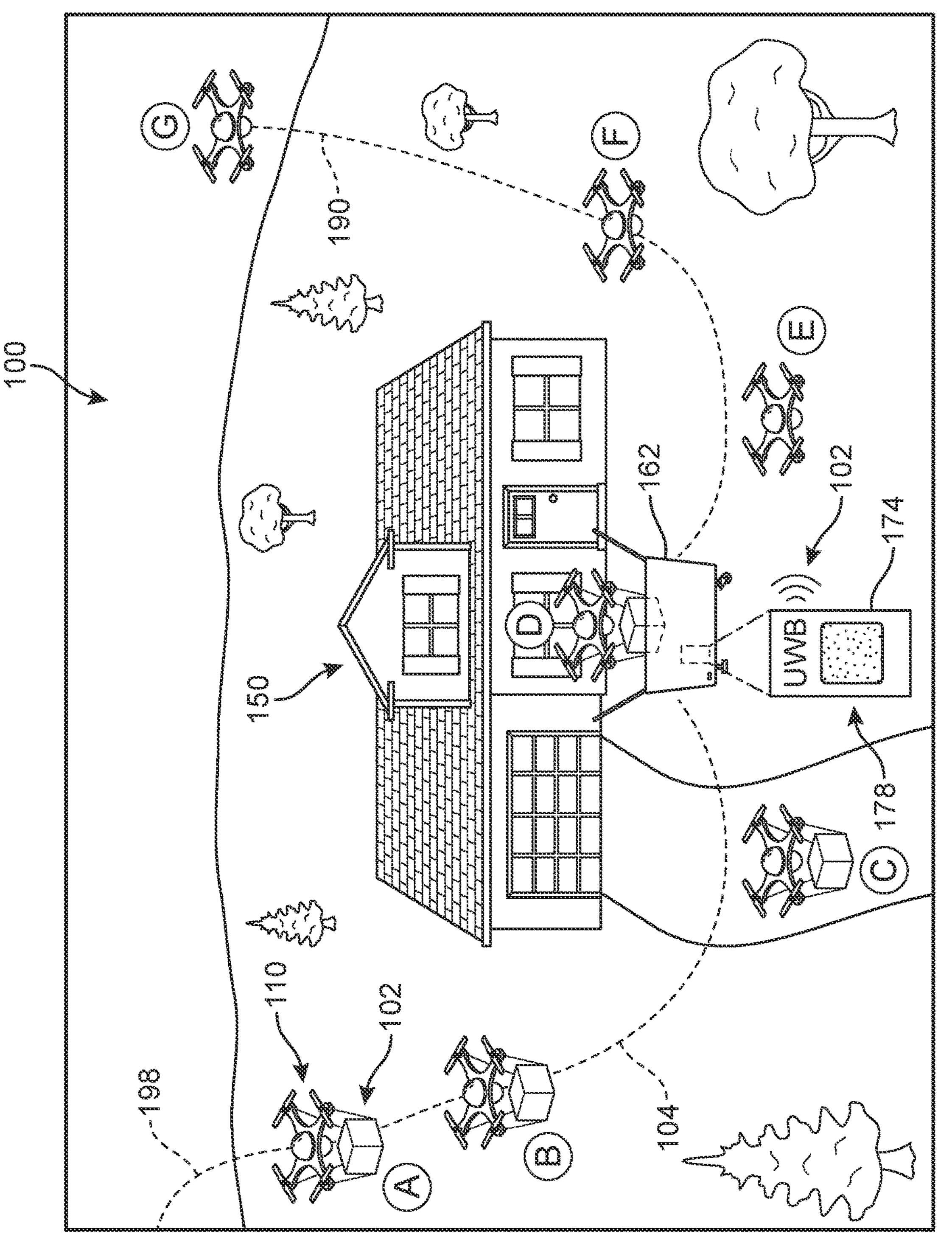
FIG. 1 is a depiction of an embodiment of a UWB-based high-precision navigation system, the system being employed by an unmanned aerial vehicle (UAV) during a delivery to a house, according to an embodiment.

Despite the simultaneously growing popularity of both unmanned vehicles (UVs) such as unmanned aerial vehicles (UAVs) and online shopping with home delivery, the issue of the "last mile" remains an obstacle to widespread implementation of a drone delivery service. Although it is believed that autonomous vehicles will deliver 80 percent of parcels in the future, there is a general belief that an autonomous drone delivery model is only viable in rural areas. The proposed embodiments describe a system and method for drone delivery that integrates with local on-site ultra-wide band (UWB)-enabled devices to provide the drone with localization, navigation, and coordination data both in and outside of rural areas. For purposes of this application, UWB refers to a radio technology that can use a very low energy level for short-range, high-bandwidth communications over a large portion of the radio spectrum. The proposed systems are configured to enable autonomous drone delivery in dense urban environments, such as neighborhoods and with buildings equipped with a small private area for landing such as a balcony or a porch. The proposed embodiments are designed to substantially expand the delivery range for drones and offer increased precision with respect to landing zones. Devices equipped or enabled with UWB technology can be referred to as UWB-enabled devices and UWB devices throughout this application.

As will be described in greater detail below, the proposed embodiments are directed to a method and system for delivering packages to precise locations at a house or other building. As noted above, conventional delivery drones are equipped to fly to a specific GPS location, also referred to herein as a macro-destination, but lack infrastructure for determining exactly where to leave a package (such as on a doorstep, porch, by a back door, etc.), referred to herein as a micro-destination. The proposed system uses devices that can communicate via UWB frequencies to help guide UAVs or even delivery persons to precise locations (micro-destinations) once they are at the specific address. Once the UAV arrives at this macro-destination, communication between the UAV and an on-site UWB device can allow the UAV to precisely navigate to the micro-destination corresponding to the UWB device. These instructions can be received by the drone to approach the drop site and also to back out by using the same path in reverse. Thus, the UAV 'switches' to this local UWB device-based navigation in order to make its final approach to the target, and switches back to its standard "macro-navigation" systems once the delivery is complete.

As one example, an apartment-dweller of a multi-story building may have a UWB device installed on their balcony in the precise spot where delivery is desired. During delivery, the UAV would use GPS to navigate to the general area where the building is located, but then switch to using the UWB localization signal to find the precise package drop-off location. In another example involving a delivery person, the driver's navigation system would use GPS to arrive at a macro-destination and then the system could switch to UWB and provide, via UWB and a mapping system, precise directions to the exact drop off location. In one embodiment, UWB routing for a delivery person is enabled as soon as they scan a package as they arrive at a particular delivery address (via GPS or general routing).

In some embodiments, the UAV itself may be equipped with a UWB device or chip. If the UAV crashes or is otherwise disabled, the onboard UWB device could be used to help locate the UAV. In some embodiments, the package itself could include a UWB device, and communication between the package's UWB device and the micro-destination's UWB device (placed to mark the precise delivery location) could be used to monitor whether or not a package may have been stolen.

In some embodiments, to enable the system, when a user orders a package, they could also provide their UWB device's signature to the routing system, so that the drone, or delivery person, could find the exact drop off location. In different embodiments, the system would offer users a specially designated container that interfaces with the delivery system. The container could be used for cleaning and/or disinfecting packages, to keep packages cold, or for other suitable purposes. The UAV (and/or a device used by a delivery person) may also be equipped with UWB, so that as the UAV or person approaches and is close enough to the container for the UWB devices to communicate, the container would automatically open. Then, once the UAV/person has moved out of the UWB communication range, the container would automatically close and secure the package.

As a general matter, UWB technology uses billions of pulses of radio that are sent every couple of nanoseconds as a pattern across a wide frequency spectrum (at least 500 MHz or 20% of the center frequency). These signals, carrying localization data (position tracking information) are dispatched from a transmitter to a receiver, or amongst transceivers. The receiving device analyzes the incoming pattern and translates it into data. While this allows devices to quickly send data over short ranges, these UWB localization signals can also be used to accurately sense the location of devices. This makes it possible for UWB-enabled devices (like smartphones or sensors and UWB anchors/tags and chips) to pinpoint a UWB transmitting device, such as another smartphone or asset tracking device, find its precise location, and in certain applications enable location-aware communication and services. Throughout this application, the term "UWB device" will be used to describe UWB transmitter-equipped devices, such as a computing device that includes a UWB tag or chip, that can be disposed on a property to signal a specific micro-destination. In different embodiments, each UWB device serves as a tracking device that emits a localization signal that can be used to determine a location. The UWB device can include a processor, a transmitter for transmitting that under control of the processor, that pings at a ping rate that are detectable by an object tracking system (e.g., a drone or delivery person), and a memory. In some embodiments, the UWB devices in this application, once installed in a specific location, can serve as UWB anchors that will transmit signals to the incoming delivery agent (e.g., carried by either a drone or delivery person) UWB device that can represent a UWB tag. In another embodiment, the UWB devices in this application, once installed in a specific location, can serve as UWB tags that will transmit signals in conjunction with UWB anchors installed (e.g., by the homeowner) elsewhere along the property to the incoming delivery agent (e.g., carried by either a drone or delivery person) UWB device that can represent a UWB signal receiver.

UWB has many unique advantages that make it highly suitable for use in drone navigation. UWB technology can transmit very high data rates over short ranges, and pinpoint exact location in real-time. UWB operates with a high bandwidth over a very wide frequency spectrum between 3.1 to 10.6 GHz. It also consumes very little power, allowing for affordable and efficient hardware options, such as tracking tags with coin cell batteries that can operate for multiple years without being recharged or replaced. UWB can precisely detect location due to its distance-based measurement via time-of-flight (ToF), that calculates location based on how long it takes for pulses of radio to travel from one device to another. UWB technology can also use Angle of Arrival (AoA) to even more precisely measure location with direction finding, which requires devices with multiple antennas that can measure the angle of an incoming signal.

Furthermore, UWB can detect the location of a device over a range under 200 meters, though it operates most effectively over short ranges, generally between 1-50 meters, and works best with line of sight between devices or tags or beacons. However, although UWB location tracking only works over shorter ranges (e.g., once the drone has arrived at the macro-destination), the location of UWB localization signals can be determined with an accuracy of less than 50 centimeters (with optimal conditions and deployment), and extremely low latency. Other standards like BLE and Wi-Fi, usually cannot be used to do this, and instead typically determine location via rather unreliable received signal strength indicators (RSSI) only showing rough categories of “weak” or “strong” received signals, which grants location accuracy into the meter level.

In different embodiments, the present disclosure uses timestamp-able signals (sometimes referred to herein as “localization signals”). Timestamp-able signals are radio frequency (RF) signals, with each signal having a feature that can be detected and that can be timestamped precisely. Examples of features include a signal peak, a signal’s leading edge, and a signal preamble. Examples of timestamp-able signals include RF signals with a distinct, well-defined, and repeatable frequency increase or frequency decrease with time. Further examples of timestamp-able signals include signal bursts, signal chirps, or signal pulses. Further examples of timestamp-able signals include signals with features suitable for phase correlation or amplitude correlation techniques (e.g., signals with codes that have low auto-correlation values). In some embodiments, the timestamp-able signal are “open-loop”, one-directional RF signals transmitted over a reception area. Some non-limiting examples include DCF77 time code signals, GPS P-code signals, and terrestrial trunked radio signals. In some embodiments, the apparatus is a non-emitting apparatus.

In some embodiments, the timestamp-able signals use a narrow frequency band. In some embodiments, a center or carrier frequency in the ISM band is used. In some embodiments, a center or carrier frequency in the range of 1 to 48 GHz is used. In some embodiments, a center or carrier frequency in the range of 2.4 to 12 GHz is used. In some embodiments, a center or carrier frequency in the range of 3.1 to 10.6 GHz is used. In some embodiments, higher frequencies are used. Narrow band signals tend to suffer from multipath fading more than wide band signals (e.g., ultra-wideband (UWB) signals). In narrow band signals, signal duration is typically longer than the delay variance of the channel. Conversely, with UWB signals the signal duration is typically less than the delay variance of the channel. For example, in the case of an UWB system with a 2 nanosecond pulse duration, the pulse duration is clearly much less than the channel delay variation. Thus, signal components can be readily resolved and UWB signals are robust to multipath fading.

Thus, for purposes of this disclosure, timestamp-able signals are UWB signals. UWB signals are spread over a large bandwidth that exceeds the lesser of 125 MHz or 5% of the arithmetic center frequency. In some embodiments, UWB signals are signals that are spread over a bandwidth that exceeds the lesser of 250 MHz or 10% of the arithmetic center frequency. In some embodiments, UWB signals are signals that are spread over a bandwidth that exceeds the lesser of 375 MHz or 15% of the arithmetic center frequency. In some embodiments, UWB signals are signals that are spread over a bandwidth that exceeds the lesser of 500 MHz or 20% of the arithmetic center frequency. In some embodiments, a bandwidth in the range of 400-1200 MHz is used. In some embodiments, a bandwidth in the range of 10-5000 MHz is used. In some embodiments, a bandwidth in the range of 50-2000 MHz is used. In some embodiments, a bandwidth in the range of 80-1000 MHz is used. Ultra-wideband technology allows an initial radio frequency (RF) signal to be spread in the frequency domain, resulting in a signal with a wider bandwidth, ordinarily wider than the frequency content of the initial signal. UWB technology is suitable for use in a localization system because it can transmit very short-duration pulses that may be used to measure the signal’s arrival time very accurately and hence allow ranging applications. UWB signals may be advantageous for use in localization systems because of their capability to penetrate obstacles and to allow ranging for hundreds of meters while not interfering with conventional narrowband and carrier waves used in the same frequency bands.

In some embodiments, a self-localizing apparatus such as an onboard computing device for a UV or a mobile computing device associated with a delivery person may be configured to receive timestamp-able localization signals. In some embodiments, the self-localizing apparatus may be further configured to determine a timestamp corresponding to the reception of the first localization signal from the UWB device and determine position information based on a known transmission time of the first timestamp-able localization signal and the timestamp. Position tracking or dynamic navigation can then be performed by a position unit configured to analyze a distance to the UWB transmitter and determine a position in space based on the distance to the UWB transmitter.

For purposes of clarity, an overview of one embodiment of the proposed systems and methods is illustrated with reference to FIG. 1. In FIG. 1, an example of an implementation of the proposed system is shown as executed via the onboard computing device of a first UAV 110 working in concert with a first ultra-wide band equipped chip ("first UWB device") 174 disposed on a property 100 (representing a type of macro-destination). In different embodiments, the first UWB device 174 includes or is associated with input and output components that provide signal receiving and transmitting capability. The property 100 in this case includes a house 150, and the first UWB device 174 is embedded, attached, adhered, or otherwise associated with a surface of a first receiving container 162 set outside a front portion 152 of the house 150. Additional details regarding the receiving container will be discussed with reference to FIGS. 7 and 8 below.

As used herein, the term "building" or "structure" can refer to any kind of building, such as a home, or other residential building, apartment complex, a shed, barn, a commercial building or any other related structures. A building typically can include a roof, room, walls, support structures, windows, or other features. In some cases, a primary structure situated on the property 100 can be associated with additional secondary structures, features, landscaping, or other real property that may be disposed adjacent to or otherwise near the primary structure. In different embodiments, the first UAV 110 is configured to navigate to the general area near the house 150, which represents the macro-destination in this example. For purposes of this discussion, a macro-destination refers to the larger target destination that can be reached without reference to a UWB device. In some embodiments, the first UAV 110 approaches a first proximate position (denoted by reference letter "A") close to the house 150. For purposes of this application, a "proximate position" refers to a position such that the first UWB device 174 associated with the property 100 is able to effectively transmit and receive information with the first UAV 110.

Once the first UAV 110 approaches and arrives at the first proximate position "A" via, for example, GPS-based navigation 198, it can initiate communication with the first UWB device 174 before beginning its 'final approach' to the micro-destination. As shown in FIG. 1, the onboard computing system for first UAV 110 has received and is executing a first route 104 that directs the first UAV 110 toward the first receiving container 162 via waypoints "B" and "C" and "D".

In this example, the first UAV 110 approaches the first receiving container 162 outside a front-facing window of the house 150. The first UWB device 174 emits a signal 176 that can be received by first UAV 110 once it is in range. The first UAV 110 then moves toward the first UWB device 174 based on the signal 176, until it hovers directly over the first receiving container 162. In response to determining the correct position has been achieved (e.g., half a meter above the UWB device, or some other positional reference as defined by the owner of the UWB device), the first UAV 110 can trigger a release of the package 102 into the first receiving container 162. Once the package 102 has been delivered, the first UAV 110 can initiate a return trip 190 to its home base or some other macro-destination, such as via waypoints "E", "F", and "G".

In different embodiments, the first UWB device 174 can be configured as a standalone navigation device that can be obtained for the primary purpose of directing UAVs to the correct micro-destination. However, in other embodiments, the first UWB device 174 is incorporated into an existing smart device, such as a smart doorbell (e.g., Ring®, Nest®, Wyze®, etc.), the receiving container, or attached to a portion of a structure.

Figure 2:
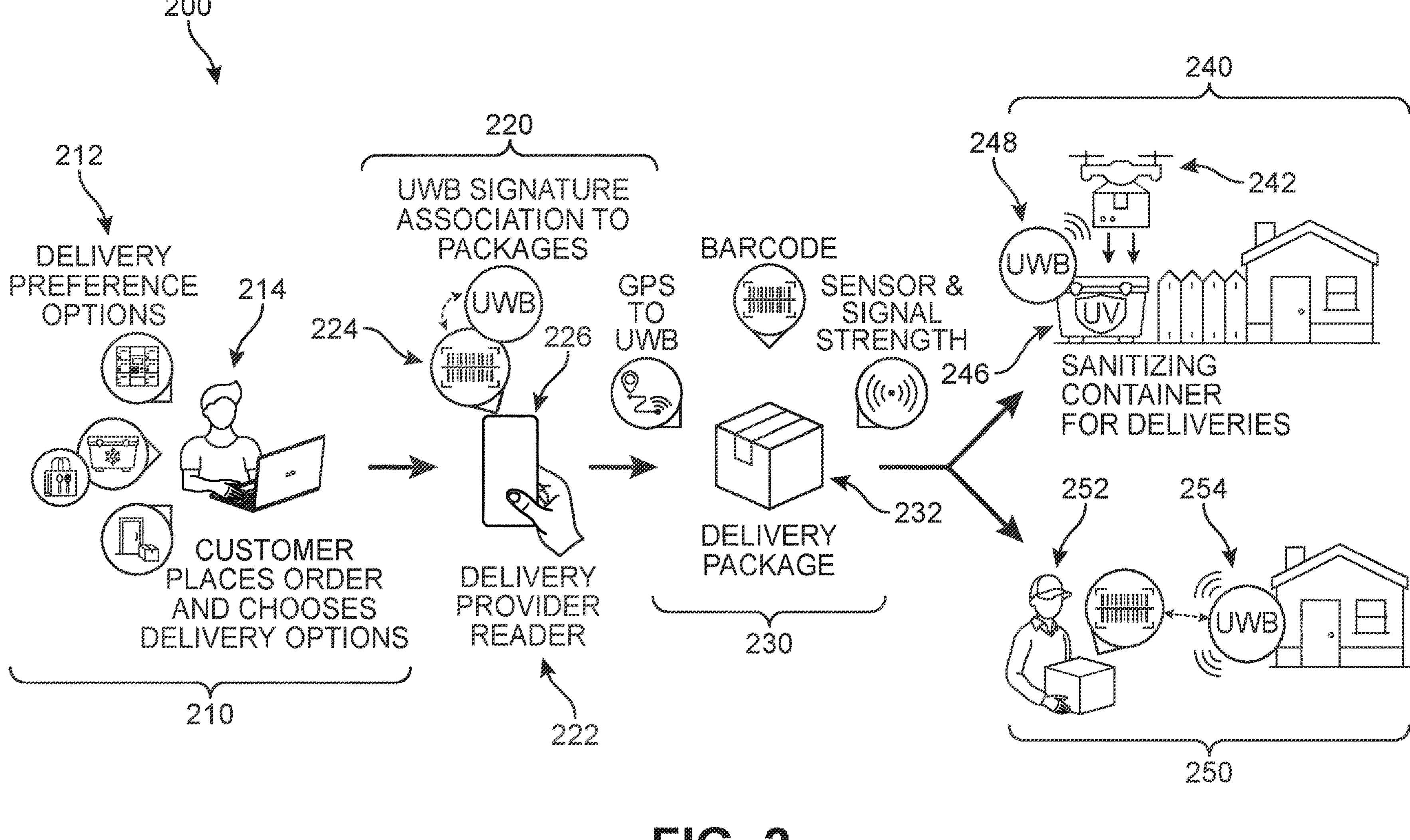
FIG. 2 is a schematic flow diagram of a process of performing high-precision deliveries, according to an embodiment.

Referring now to FIG. 2, a schematic diagram of a process 200 for providing delivery service agents (e.g., drones and/or delivery persons) precise navigation guidance is depicted. In a first stage 210, a consumer 214 is shown placing an order for an item via a computing device. During this transaction, the system can present one or more delivery options 212, such as a "hub" or central pick-up location (e.g., Amazon® Hub Lockers), a secure receiving container, or direct delivery to their home or other location. For purposes of this example, the consumer 214 selects delivery to their home. In response, the system can ask the consumer 214 whether they will be using a UWB device, and if so, to enter the UWB device's information.

In a second stage 220, a delivery provider 226, using a reader 222, will scan an identification code printed on the package for the item and link 224 or otherwise associate the package with the consumer's selected or registered UWB device. In a third stage 230, a delivery service 232 will initiate transport of the package to the consumer's address. For example, GPS technology can be used to guide the delivery of the package (via a delivery person or a drone) to the address (macro-destination). In addition, once the package has come into proximity of the address, the barcode or other identification code on the package will be scanned by a UWB-enabled computing device to locate the correct UWB device. In cases where the delivery is performed by a drone 242—as illustrated in a fourth stage 240—the onboard computing system for the drone 242 can be configured to detect the transmission from a first target UWB device 248. In this example, the first target UWB device is disposed in a second receiving container 246, which may further be configured to apply sanitization techniques, as well as storage cooling/heating systems based on the conditions needed for optimal storage of the enclosed item (e.g., see FIGS. 8A and 8B). Once the drone 242 is in position, the package will be deposited safely into the second receiving container 246. In another embodiment—as illustrated by a fifth stage 250—a portable computing device used by a delivery person 252 can be used to hone in on a second target UWB device 254 that was linked to the identification code to allow for manual delivery of the package to the correct micro-destination (e.g., see FIG. 9).

Figure 3:
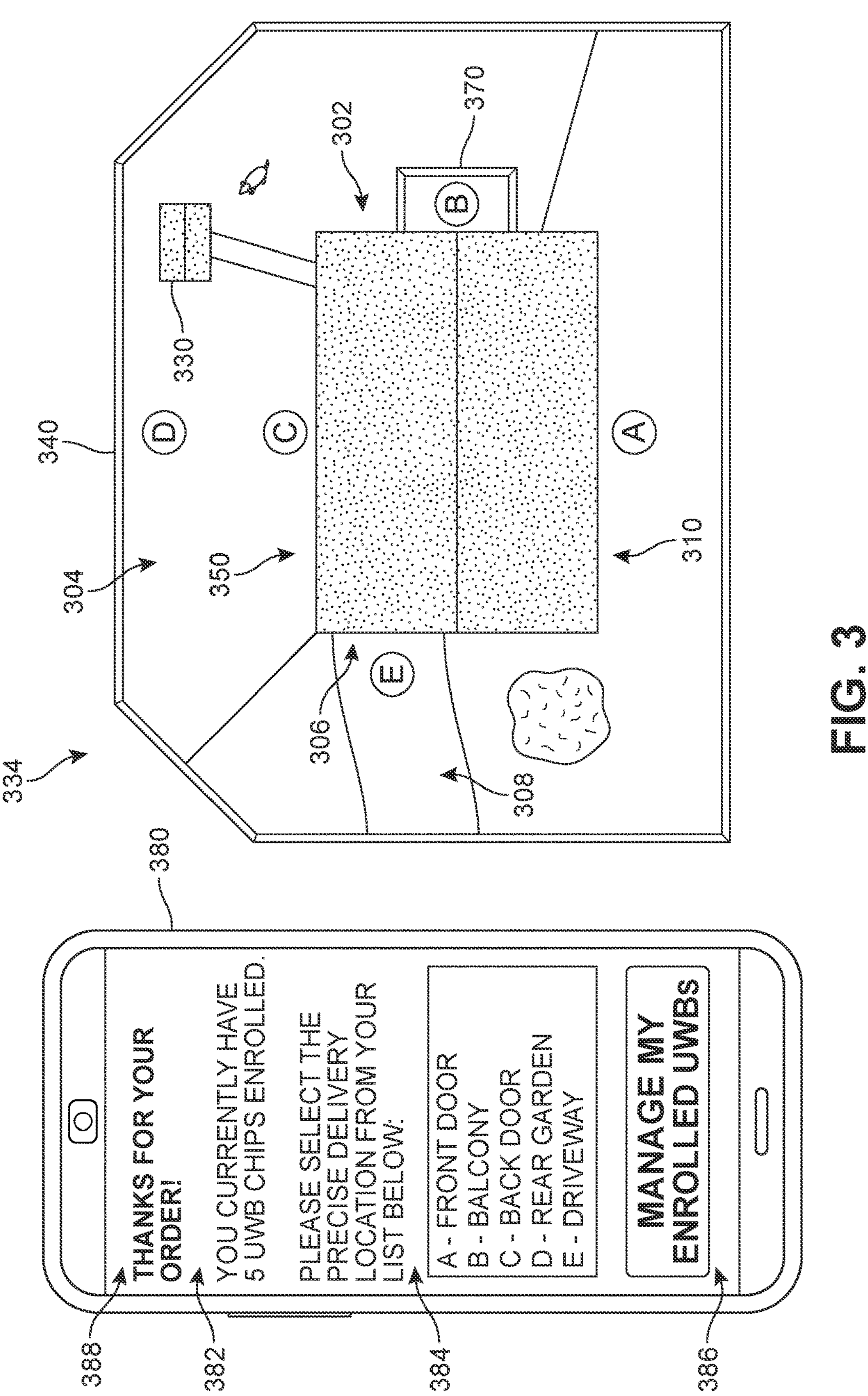
FIG. 3 shows an example of a user interface for selection of a UWB device, alongside a corresponding top-down view of a property on which multiple UWB devices are disposed, according to an embodiment.
Figure 4:
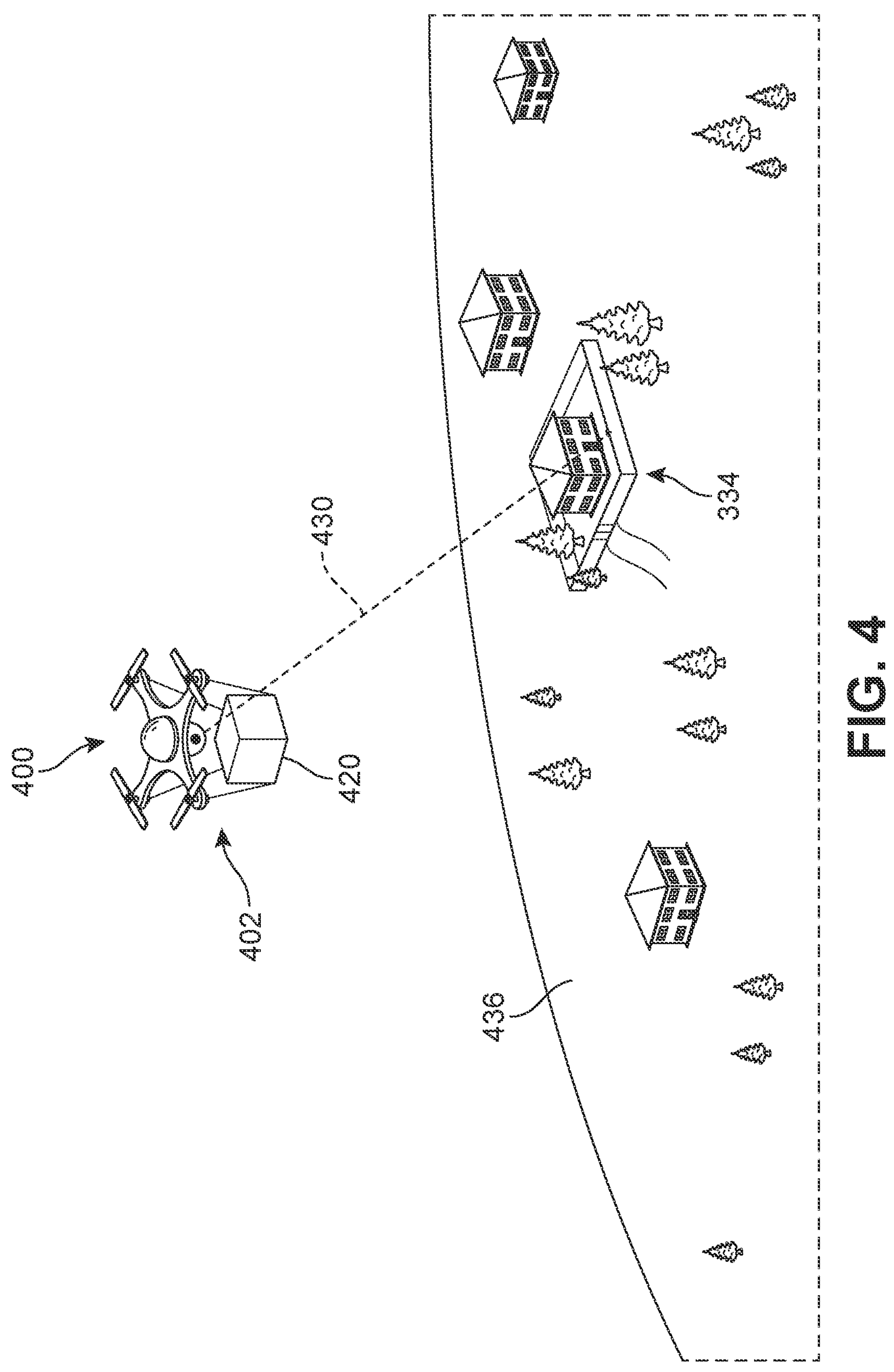
FIG. 4 is an example of a UAV approaching a neighborhood using standard navigation systems, according to an embodiment.
Figure 5:
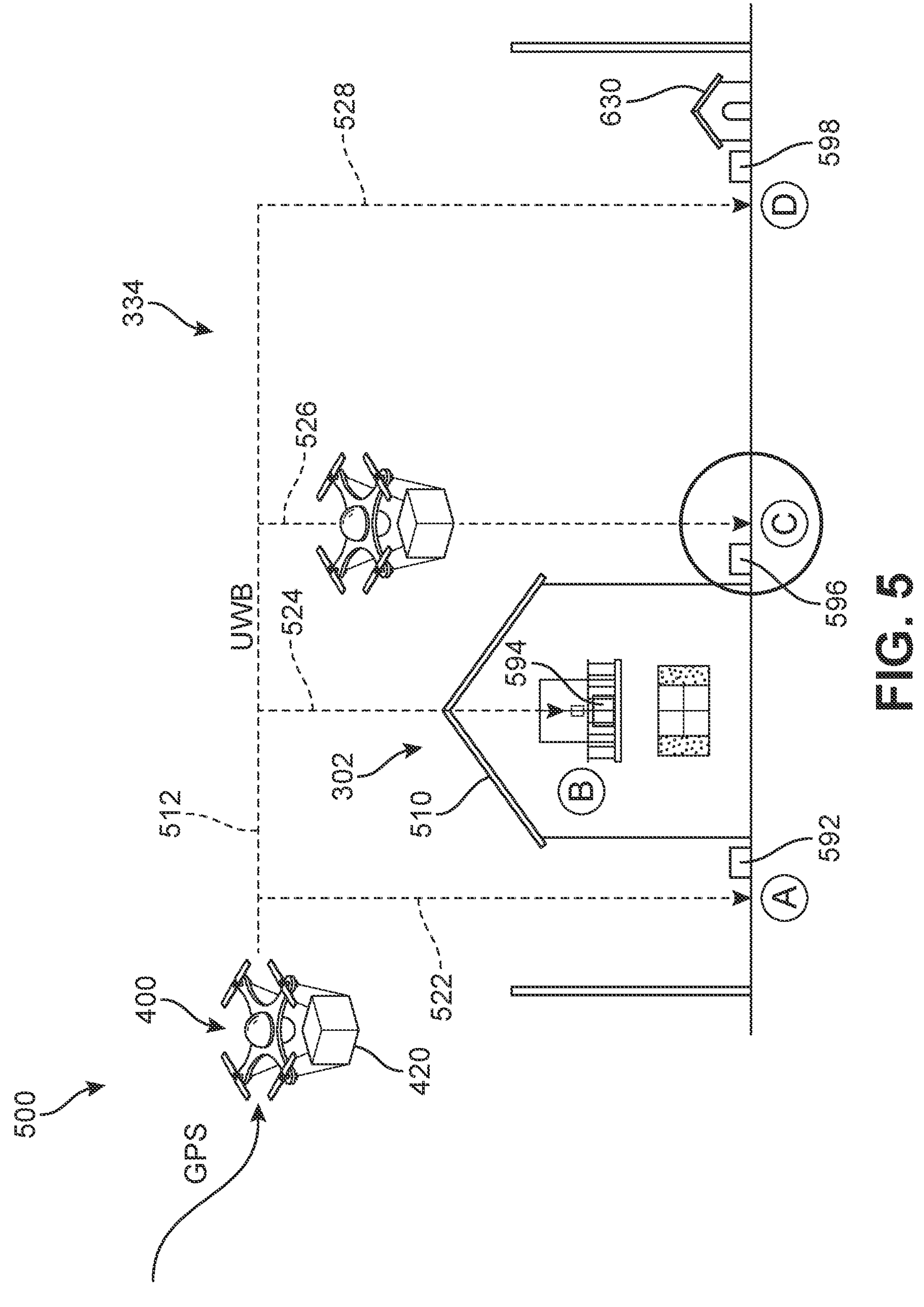
FIG. 5 is an example of the UAV having arrived at a macro-destination and preparing to hone in on a pre-designated UWB device, according to an embodiment.

Referring next to FIGS. 3-5, one example of an implementation of the proposed embodiments is depicted. In FIG. 3, a consumer (e.g., consumer 214 of FIG. 2) has placed an order with a merchant who is enrolled with the UWB-chip-based delivery system. The system can in some embodiments offer users access to UWB delivery management options via a delivery management app 388, presented in FIG. 3 on a computing device 380. In different embodiments, delivery management app 388 can be accessed over a network. in some embodiments, the computing device 380 refers to a computing device such as a laptop, desktop, tablet, mobile device, smart phone, or other computer that is configured to communicate with a remote server to make selections regarding package delivery. The computing device 380 may include one or more processors and memory. Memory may comprise a non-transitory computer readable medium. Instructions stored within memory may be executed by the one or more processors. In addition, each device may include a communication system such as a radio or other provisions for communicating using one or more communication methods. In particular, communication system includes provisions for communicating with other nearby devices and/or cloud server over a network. For example, each communication system could include a Wi-Fi radio, a Bluetooth radio, other NFC components, and/or a cellular network radio. Each computing device can include provisions for communicating with, and processing information from, a cloud-based server as well as other devices in the home network. In some embodiments, the delivery management app 388 is configured to provide controls for an end-user to adjust the parameters for delivery and/or add, delete, or otherwise modify the registered UWB-devices that are associated with the end-user and/or a specific address (macro-destination).

In FIG. 3, the delivery management app 388 displays a delivery selection page 382 ("Thanks for your order! You currently have 5 UWB chips enrolled.") which may be presented following the completion of an order with the merchant, or the end-user/consumer may be redirected to this page following the order confirmation or during the ordering process. In different embodiments, the delivery management app 388 can allow the user to enroll or register one or more UWB-enabled transmitters that can be stored in the app under their account for quick selection following a shopping transaction. During the enrollment, a unique identifier (e.g., the unique UWB chip tag/anchor address or code) for each UWB device will be inputted by the user into the app. This identifier will correspond to a single, unique UWB device associated with the user's account. In some embodiments, the UWB devices can be organized to reflect different addresses associated with the user. Thus, one or more UWB devices can be assigned to a "HOME" location, one or more UWB devices can be assigned to a "WORK" location, one or more UWB devices can be assigned a "MOM" location, etc. The user can navigate the menu to select the address and also select a UWB device associated with the selected address that corresponds to the desired micro-destination for the selected address. Furthermore, the app can allow the user to add/delete UWB devices as needed, or modify UWB device names and information if the UWB devices are moved between one address or another, or from one micro-destination to another, for example via selection of a manager option 386 ("Manage my enrolled UWBs") that can open a new page showing an interactive UWB directory for the user's account.

In some embodiments, the delivery management app 388 can also be configured to allow the user to choose a specific UWB device from their own inventory that will be linked to their order (e.g., see second stage 220 in FIG. 2). In this example, a selection menu 384 ("Please select the precise delivery location from your list below: (A) front door; (B) balcony; (C) back door; (D) rear garden; (E) driveway") is provided. Thus, it can be seen that the user can optionally nickname each of their UWB devices to indicate the particular location of each UWB device relative to a single address or structure, or to otherwise differentiate each UWB device for their own reference.

For purposes of clarity, each of the registered UWB devices shown in the selection menu 384 is represented in FIG. 3 by a top-down view of a consumer property 334 with a letter that matches and denotes the listed UWB device. Thus, the letter "A" denotes a first UWB device that has been disposed adjacent to or along a front side 310 of a residence 302 (near the front door), a letter "B" denotes a second UWB device that has been disposed on a balcony 370 protruding from a first side of the residence 302, a letter "C" denotes a third UWB device that has been disposed on a rear side 350 of the residence 302 (near the back door), a letter "D" denotes a fourth UWB device that has been disposed toward a rear area 304 of the property 334 near a fence 340 and doghouse 330 (in the rear garden), and a letter "E" denotes a fifth UWB device that has been disposed along a second side 306 near a garage door and adjacent to or on a driveway 308 of residence 302. Thus, the user account for the current transaction is employing five different UWB devices to pinpoint five different micro-destinations in one property (macro-destination).

In FIG. 4, the subsequent travel of a package 420 corresponding to the requested item is depicted as carried by a second UAV 400. The second UAV 400 is shown in a first location 402 flying over a neighborhood 436 and approaching the consumer property 334. The second UAV 400 can continue to rely on conventional navigation systems until arriving close enough to the property so as to detect the signals emitted by the on-site UWB devices. In different embodiments, the UAV can be remotely controlled or autonomously controlled.

In one example, the navigation system can include a ground system or other remote computing system that is in communication with an onboard system. In some embodiments, the ground system includes provisions for gathering information about upcoming or pending deliveries following an order request that can be used to facilitate the drone's flight through upper airspace. For purposes of this application, upper airspace refers to the navigable airspace through which a drone may travel using GIS or GPS navigation until reaching its macro-destination. Upper airspace is typically controlled. The term lower airspace, as used in this application, refers to the airspace that must be traversed in order to move to the final micro-destination (after reaching the macro-destination). Thus, in lower space, the drone will rely on navigation data received from the UWB device.

In different embodiments, the ground system comprises a computing system with one or more processors and memory. The ground system includes provisions for communicating with various other systems (e.g., a ground communication system) as well as for processing image or other data received from UAVs. The ground system can also include a path planning module that works in conjunction with a navigation module of the UAV. The path planning module includes provisions for generating upper airspace flight path directions and guidance. The drone computing system can also include a navigation module that can further include a GPS receiver for receiving GPS information that can be used to determine a GPS location for the UAV. In addition, the navigation module can receive path instructions from a ground system and process and execute the instructions to direct the UAV to an address. The UAV may also include sensors for measuring orientation, altitude, and/or acceleration. For example, the drone can include a gyroscope, an altimeter, and an accelerometer. In some embodiments, the drone can include an altitude and heading reference system (AHRS). Using these devices, the orientation, heading, and height of the aerial vehicle can be determined. This information, when used with a GPS location for the UAV, can be used to infer the location of the UAV and its position relative to a target destination.

The UAV can include a UAV communication system for communication with the ground communication system and UWB devices. These communication components enable information to be transmitted between the systems via a network or signal processing. Thus, the type of communication components used in each communication system can be selected according to the type of communication channel used. In some cases, a cellular network could be used so that each communication system includes a cellular radio or other component that enables cellular communication. Using a cellular network may enable information to be exchanged while drone is in the air where Wi-Fi or other networks might be unavailable. In other cases, networks could comprise any kind of local area network and/or wide area network. In some cases, network may be a Wi-Fi network or RF network.

In different embodiments, the UAV coverage path is composed of a set of waypoints, where each waypoint represents a navigation command to the vehicle, such as take-off, change of speed or move to a specific location, and contains information about the latitude, longitude and altitude. In one embodiment, the flight paths are typically followed by implementing guidance systems such as discrete sets of waypoints that are usually generated on a remote ground station and then wirelessly relayed to the UAV's autopilot. These waypoints have all the necessary localization information to guide the vehicle. More specifically, a waypoint at a minimum refers to data that includes a set of coordinates that identify a specific point in physical space. A ground system equipped with waypoint technology typically utilizes Global Positioning System (GPS) and Global Navigation Satellite System (GLONASS) to create waypoints. As long as the UAV is able to connect with at least four GPS or GLONASS, precise three-dimensional positioning (longitude, latitude, altitude) can be determined. Thus, waypoints can be used to describe the flight path from the drone starting point to a macro-destination. In some embodiments, a waypoint may further include instructions for the flight path between two sets of coordinates and the maneuvers that should be performed by the UAV between each set of coordinates. Furthermore, the position of the waypoint also determines the arrival time accuracy.

Referring now to FIG. 5, a side view of the property 334 and residence 302 is shown, as second UAV 400 is positioned at a macro-destination 500 near a roof 510 of the residence 302, which it has arrived at using GPS or other conventional systems. In different embodiments, one or more of the UWB devices can be configured to transmit a signal, which is received by the drone computing device. In this illustration, the letters A-E (in this case missing E, which is on the opposing side of the structure and therefore blocked from view) are again used to indicate the location of each UWB device. For example, A refers to a first UWB device 592 near the front door, B to a second UWB device 594 on the balcony on the side of the house, C to a third UWB device 596 at the back door, and D to a fourth UWB device 598 in the rear garden. Depending on the selected target, the second UAV 400 can now follow one of an array of micro-paths, including a first path 522 to the first UWB device 592, a second path 524 to the second UWB device 594, a third path 526 to the third UWB device 596, and a fourth path 528 to the fourth UWB device 598. As shown in FIG. 3, for purposes of this example, the consumer had selected a micro-destination corresponding to "C" at the back door. Thus, while there are multiple possible paths that lead to each UWB device-based micro-destination, the onboard computing system for the second UAV 400 detects and selects the UWB device address for "C" and initiates travel along the third path 526, at the end of which it will deposit its package 420 at the precise target associated with the third UWB device 596 and complete its delivery. In some embodiments, the second UAV 400 can then transmit a message to its ground system and/or the recipient's other computing devices to confirm delivery. The onboard navigation system then guides the UAV over the fence out of the neighborhood to its next destination.

In different embodiments, the UAV includes provisions to discriminate between multiple UWB signals in the same area of the delivery. As shown in FIG. 5, it can be appreciated that the UAV must also perform a process of identifying and homing in on a specific UWB device when approaching a home or a large building with multiple UWB signals. For example, in some embodiments, the proposed embodiments offer a location-based service (LBS) using a ultra-wideband (UWB) signal in which the delivery agent device scans for UWB devices in the vicinity of the delivery location and has a corresponding unique identifier that was provided by the customer. In one embodiment, the systems and methods disclosed herein incorporate an LBS using a UWB signal that is unique and can be pinpointed or selected from among a plurality of other UWB signals that may be in range of the receiver.

Figure 6:
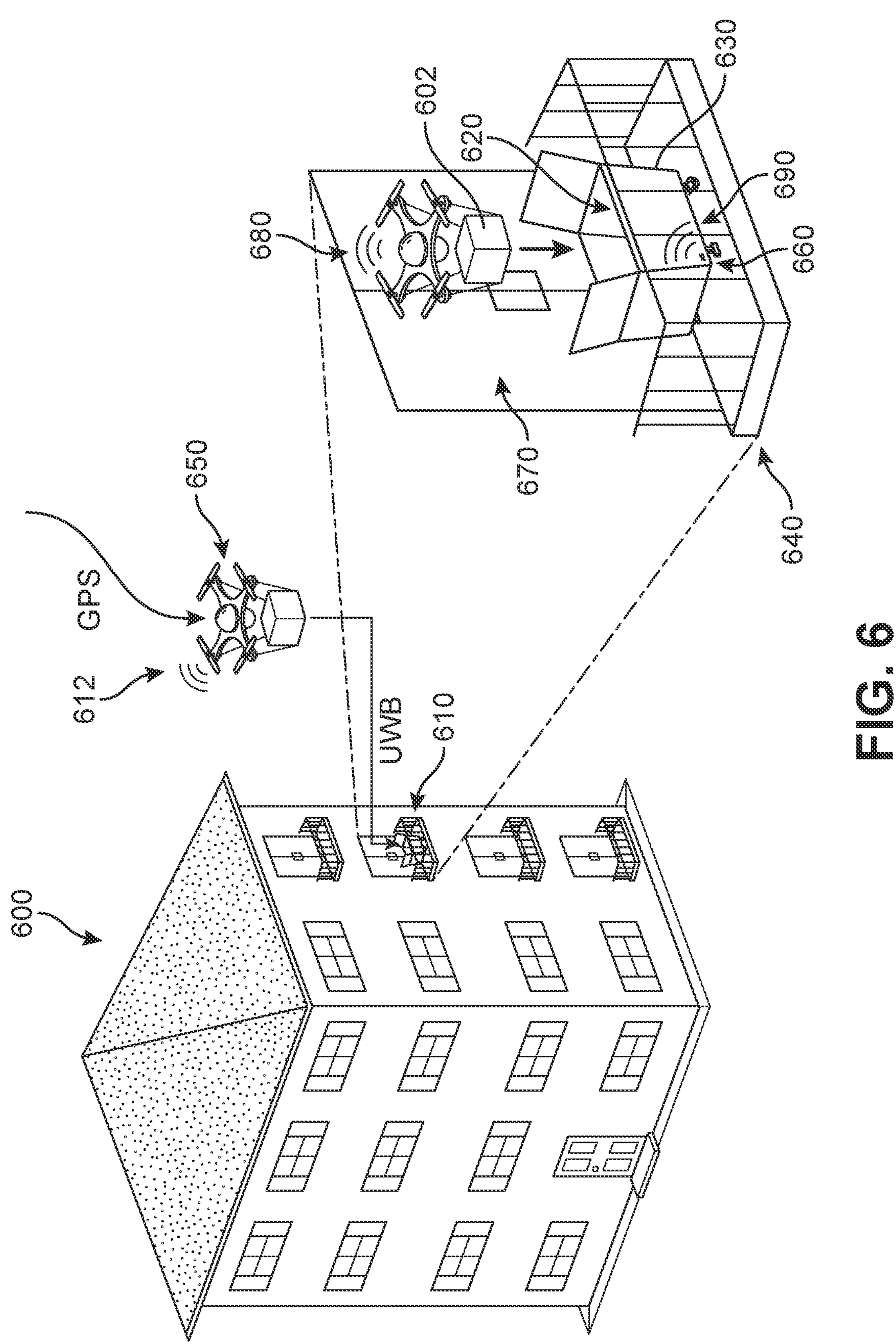
FIG. 6 is a depiction of a UAV performing a delivery to a specific target apartment at an apartment building based on a UWB device disposed on its balcony, according to an embodiment.

As another example, FIG. 6 shows a large apartment building 600 comprising multiple apartments, with a first apartment dwelling 610 having placed a UWB device 660 directly on their balcony 640 (see enlarged view). In this case, the UWB device 660 is installed or otherwise incorporated into a delivery container 630 that has been set outside on their balcony 640 adjacent to sliding doors 670. As a third UAV 650 approaches building macro-destination 612 via a GPS or GNSS-enabled path, it receives 680 a first localization signal 690 being transmitted from the UWB device 660. The second UAV 650 attains the pre-defined point relative to the UWB device 660 and drops its package into an interior camber 620 for the secure container 630. The third UAV 650 can then return to airspace to travel to its next destination.

Figure 7:
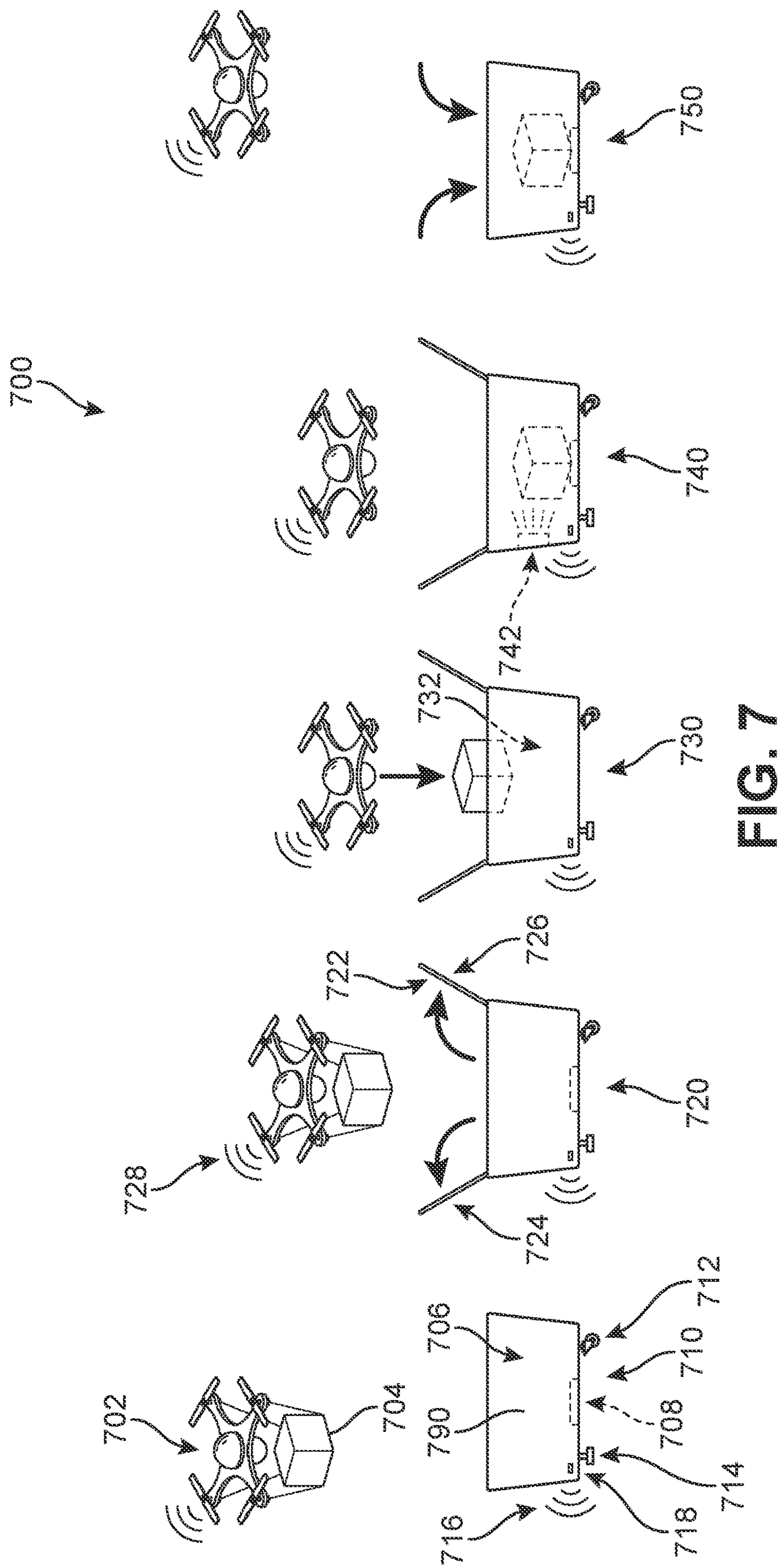
FIG. 7 is a schematic sequence showing a process of releasing a package into a secure smart container system, according to an embodiment.

Further information regarding embodiments of the specialized delivery containers will now be provided with reference to FIGS. 7 and 8A-8C. In FIG. 7, a schematic diagram illustrating a process of a fourth UAV 702 interacting with a first smart delivery container system ("first container") 706 is shown. At a first stage 710, the fourth UAV 702, transporting a parcel 704, is shown approaching the first container 706. In this example, the first container 706 can be seen to comprise a substantially rectangular prism-shaped housing 790 surrounding an inner chamber 732, though in other embodiments its outer three-dimensional shape can vary. The first container 706 further includes a UWB device 708 that produces a first localization signal 716 that will be received by the fourth UAV 702. In some embodiments, first container 706 also includes a charging port 718 accessible from an external or outwardly-facing surface or portion of the housing. Furthermore, in optional embodiments, the first container 706 can include provisions for mobilizing and/or stabilizing the container housing, such as a rotatable set of rear wheels 712 and a set of feet 714.

In a second stage 720, the fourth UAV 702 has received the first localization signal 716 and is emitting its own second signal 728 that includes an access signature. In response to the second signal 728, which serves as a triggering signal or verification signal, the first container 706 unlocks and activates a door opening mechanism, causing a set of doors ("doors") 722 (here shown as a first door 724 and a second door 726) to open. Although the doors 722 are shown as hingedly connected to the peripheral sides of the first container 706 and therefore swing outward to either side when opening, in other embodiments, each of the doors may be associated with a roll (coiling-up) mechanism incorporated into the first container 706, such as a wheel and tracks and roller, as well as a spool. In other words, each door may roll into a hollow section or compartment formed on both sides of the container in a manner similar to a garage door. In other embodiments, there may only be a single door or lid that slides horizontally open, or a single door that swings open to one side or rolls into the side compartment.

In a third stage 730, the onboard computing system for fourth UAV 702 determines based on sensor data (e.g., cameras, etc.) that the doors have been opened and interior chamber 732 is exposed or accessible via an opening. Once the fourth UAV 702 is in the correct position relative to the opening and the UWB device 708, the parcel 704 can be automatically released and dropped into the interior chamber 732. The first container 706 now securely holds the parcel 704 in a fourth stage 740, and may apply various sanitization techniques (disinfectant spray, UV light, etc.) via components 742 installed in the housing that are configured to activate automatically in response to sensor detecting a weighted object being disposed on a bottom floor of the housing. Finally, in a fifth stage 750, the fourth UAV 702 is shown departing, while the doors 722 reseal or close automatically to secure the parcel 704 from unauthorized access. The first container 706 can be opened by the owner by way of a signal received from a computing device logged into the delivery management app, a key in a lock (not shown), or a passcode or other biometric identification scanned by a secured entry system for the container (not shown).

Figure 8B:
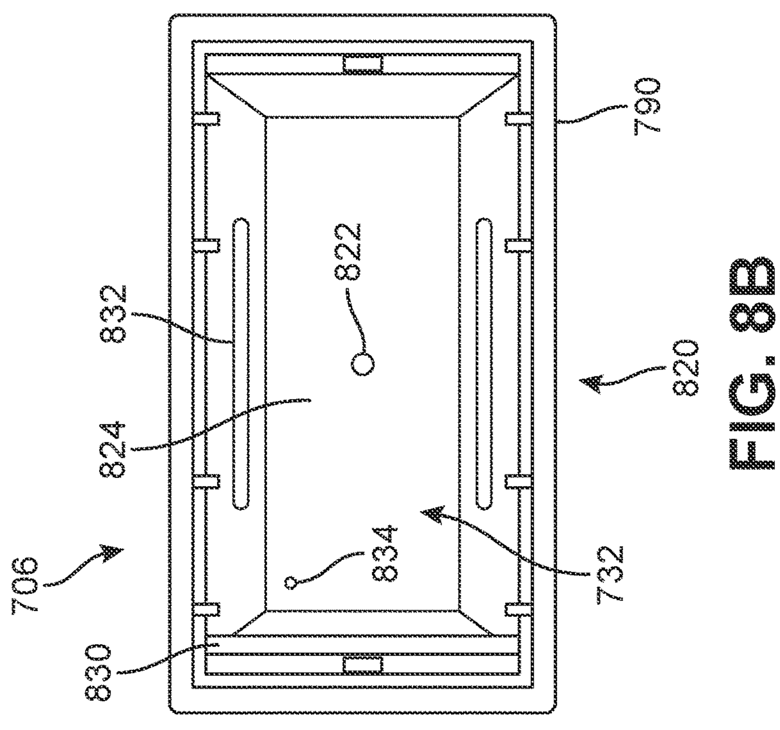
FIGS. 8A and 8B are top-down schematic views of an example of a smart container system, according to an embodiment.
Figure 8A:
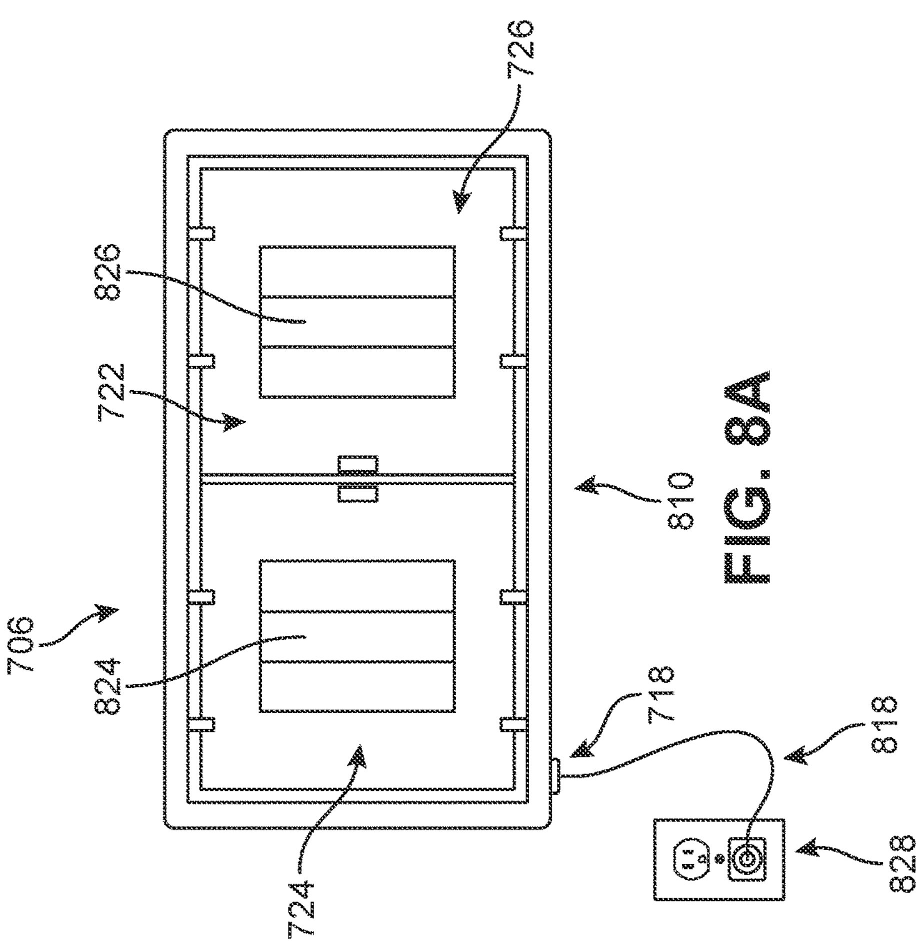

Additional details regarding first container 706 are now provided with reference to FIGS. 8A and 8B. In FIG. 8A, a top-down view of the first container 706 in a closed (secured) configuration 810 is depicted, and in FIG. 8B, a top-down view of the first container 706 in the opened (unsecured) configuration 820 is depicted. It should be appreciated that the size and dimensions of the container can vary and the owner can purchase a container in the shape and size that is most suitable for their needs. Typically, the container will provide an interior volume sufficient to receive standard package sizes and boxes. In different embodiments, the container can include provisions for charging or otherwise receiving power for onboard operations such as door openings/closings, sanitization functions, security protocols, lighting elements, computing devices, UWB device, temperature settings (e.g., A/C), and sensor operations. For example, some external portions of the container, such as doors 722, can include solar panels (here shown as a first solar panel 824 installed on the first door 724 and a second solar panel 826 installed on the second door 726) that can recharge an onboard rechargeable battery. In another embodiment, charging port 718 can be connected by a wire 818 to a charging station 828 to recharge the battery or provide a continuous power supply in cases in which there is no onboard battery. Furthermore, in some embodiments, the first container 706 includes one or more heating and/or cooling elements that can be used to control the temperature in cases in which the package is temperature-sensitive. In addition, in different embodiments, the container can be buoyant and waterproof in case of flooding in the region.

In FIG. 8B, some of the optional onboard features disposed along the interior chamber 732 can be observed. For example, a leak detection sensor 834 can be incorporated, attached, or embedded into a floor bottom 824 of the housing 790. The leak detection sensor 834 can determine if a moisture content level or fluid level in the interior chamber 732 has exceeded a threshold, which can trigger an automatic alert to be presented to the container owner via the app, text, email, or phone call. In addition, a UWB device 822 is also disposed, attached, incorporated, or embedded in or on the bottom floor 822. In one example, the UWB device 822 is removable and fits into a pre-formed slot in the bottom floor 822, and can be readily replaced or updated. In another embodiment, a plurality of sanitization elements 832 (e.g., UV lights or disinfectant sprayers) are mounted on the inner sidewalls. In some embodiments, the sanitization elements 832 are configured to automatically turn on for some predefined period of time in response to a door open/close cycle. In another example, a lighting element may be installed in the interior chamber or the exterior of the housing that automatically turns on as the doors open and turns off once the doors have closed. Furthermore, in some embodiments, the first container 706 includes secondary doors directly below the primary doors (i.e., doors 722 in FIG. 8A) that are sealed when additional insulation is needed for the contents of the parcel.

In different embodiments, a container-based computing system is also included in the smart container system. The computing system can be connected to one or more sensor devices in addition to the leak detection sensor. Some non-limiting examples of such sensors include (a) Smoke, Gas and Alcohol (and/or other chemicals) sensors; (b) Temperature sensors; (c) Pressure sensors; (d) Cameras and other image and/or light sensors; (e) Smoke/Flame sensors; (f) Moisture/Humidity sensors; (g) Electrostatic sensors; (h) Audio sensors and other sound/volume sensors (e.g., microphones); (i) Motion/speed sensors; (j) Gyroscopes; (k) Accelerometers; (l) Wind Speed sensors; (m) Proximity sensors; (n) Infrared and Heat sensors; (o) weight sensors; and (p) security sensors that detect whether the container is open or closed. In addition, in some embodiments, sensors can include ultrasonic sensors, touch sensors, aerosol characterization sensors, magnetometers, color sensors, tilt sensors, and flow and level sensors. Thus, in different embodiments, sensor devices may collect data regarding relative location, direction, weight, size of the package and/or of environmental conditions inside the interior chamber as well as around the container (external environment). In cases in which temperature sensors are included, the system can be configured to also monitor the temperatures of packages left inside the container, or infrared data can be used to help determine a likely stability level for a structure or potential internal damage.

Figure 8C:
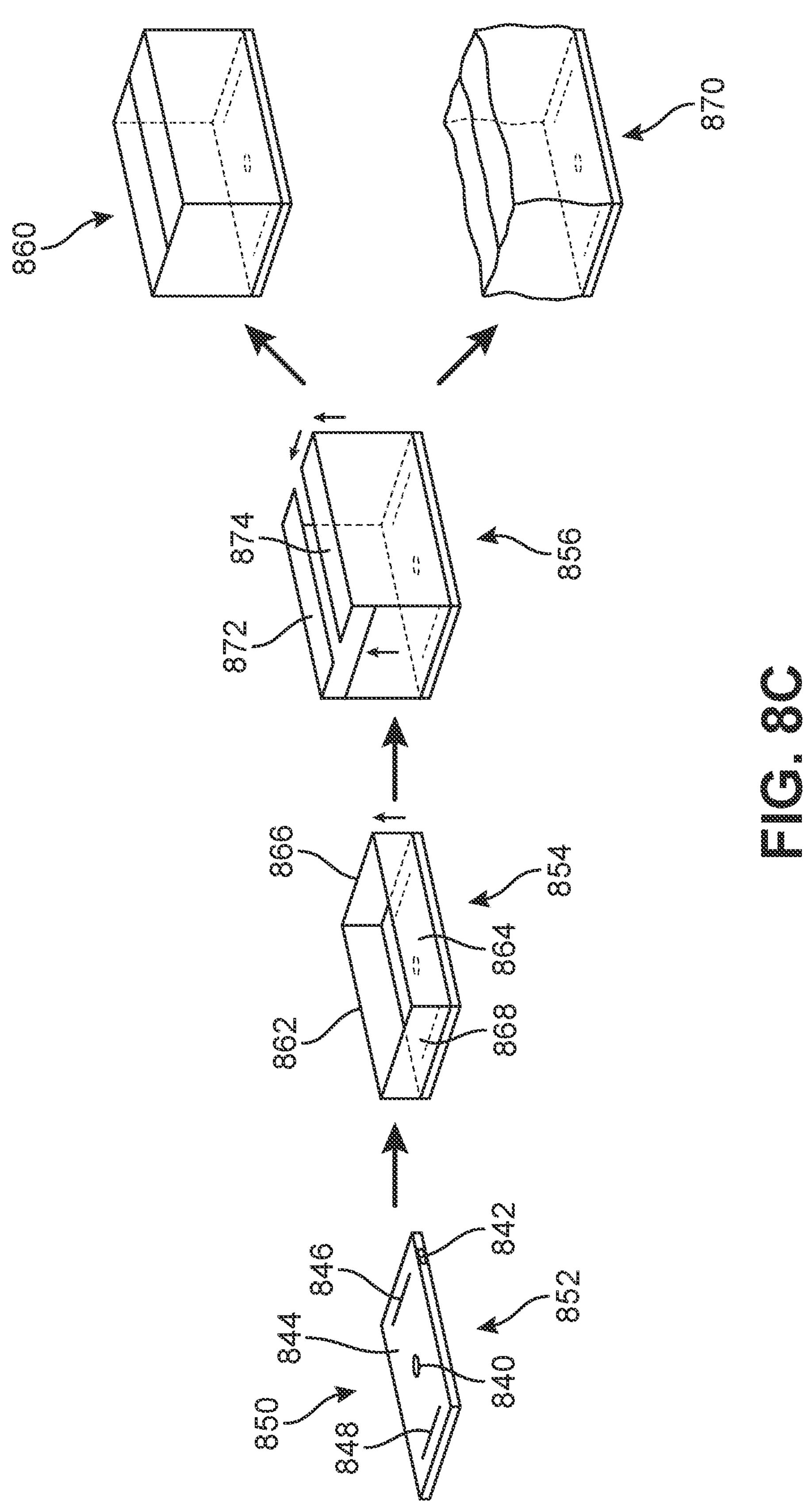
FIG. 8C is a schematic sequence showing another example of a smart container system transitioning from a retracted state to a deployed state, according to an embodiment.

As an alternative example of a receiving system, a second smart delivery container system ("second container") 850 is presented in FIG. 8C in a schematic flow diagram. The second container 850 includes a collapsible platform, initially shown in its retracted or compact state in a first phase 852. The second container 850 can be seen to include a base 844 which holds or represents the system in its entirety. A UWB device 840 is installed or embedded in a topside of the base 844, as well as optional UV lights (first light 846 and second light 848) at each of its two end regions. The UV lights can automatically turn on following each transition from the retracted state to the expanded or deployed state. In addition, similar to the charging port 718 of first container 706 in FIG. 8A, a charging port 842 can be provided on an exterior-facing side surface of the base 844.

In a second phase 854, from a peripheral portion of each of the four sides of the base 844, container walls stored within compartments formed in the underside of the base 844 begin to emerge. In some embodiments, the second phase 854 is automatically triggered in response to the delivery of a package onto the base 844. As shown in the second phase 854, a first sidewall 866 and a second sidewall 868 are rising on two opposing sides of the base 844, while a front wall 864 and a rear wall 862 are also rising upward. In a third phase 856, the front wall 864 and rear wall 862 have reached a top height, and two lid portions collapse inward to form a securable opening. In this case, the front wall 864 provides a first lid portion 874 and the rear wall 862 provides a second lid portion 872 that approach one another until forming a seal. Similarly, the first sidewall 866 and second sidewall 868 continue upward until meeting with the outer edges of each lid portion, also forming a seal, thereby covering or enclosing any package disposed within. In different embodiments, the resultant container can comprise a hard-shell container 860 or a soft-shell container 870, depending on the surrounding temperature.

Figure 9:
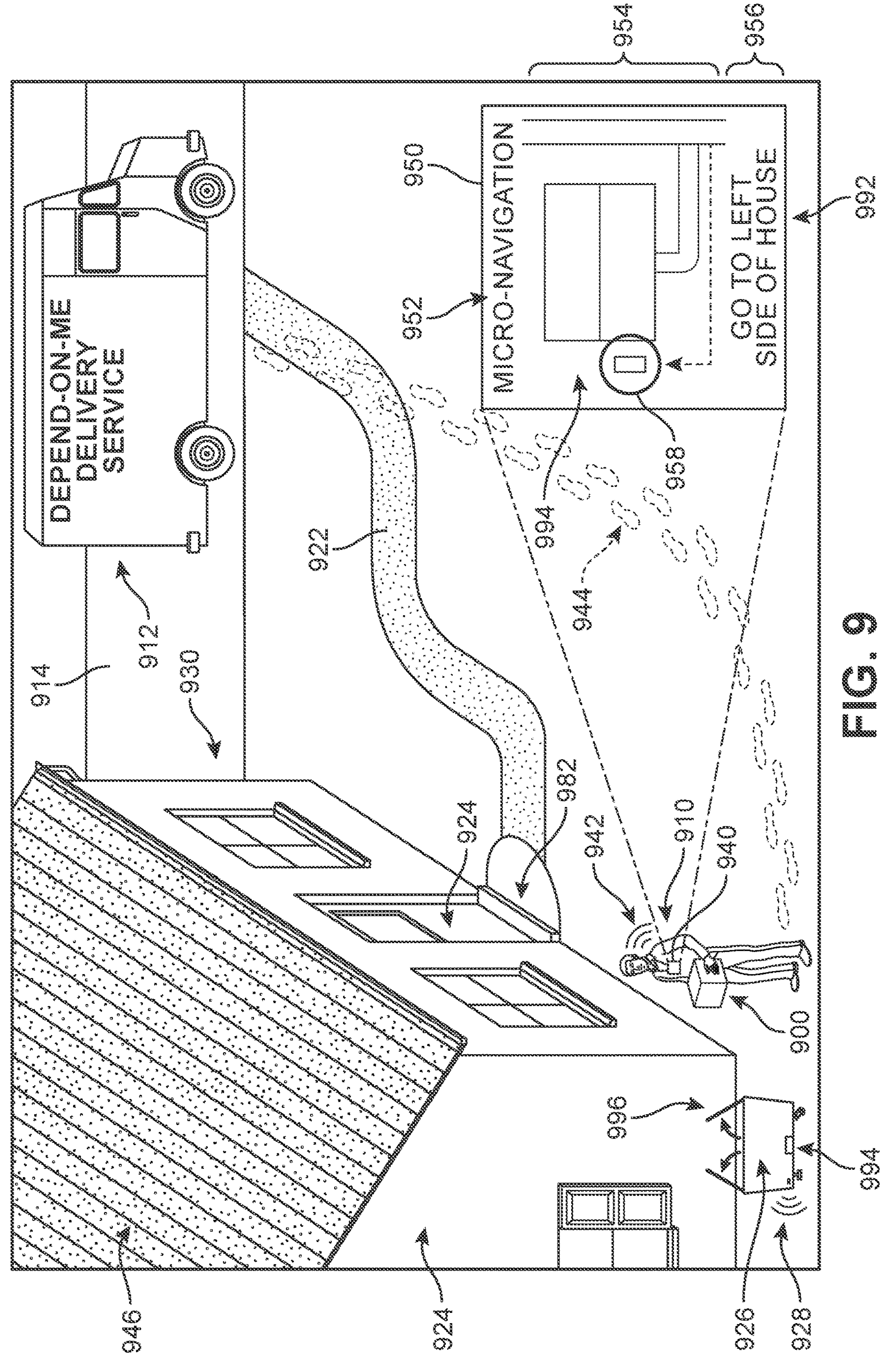
FIG. 9 is an example of a delivery person performing a delivery to a smart container system on a property, according to an embodiment.

As noted earlier, the proposed embodiments can also be implemented with person-based (manual) delivery systems. One example of such a scenario is shown in FIG. 9, where a delivery truck 912 has arrived at an address 930 via a first road 914. A delivery person 910 is carrying a package 900 assigned for delivery to the address 930, specifically to a micro-destination corresponding to a UWB device registered to the recipient and selected during the ordering of the item. The delivery person 910 walks from the truck 912 and across a front walkway 922 that is arranged to lead to a front door 920 of house 946.

However, rather than continue along the front walkway 922 (as would occur in standard delivery situations, where the package 900 would simply be left out in the open on a front porch 982), the delivery person 910 follows an alternative path 944 based on navigation guidance 952 being generated by an app 950 running on a mobile computing device 940 (e.g., a tablet or mobile phone with a network connection). This navigation guidance 952 is generated using a UWB localization signal 928 being emitted by a UWB device 994 located on-site at the address 930. It can be seen in a magnified view 992 of the mobile computing device 940 that the app 950 as presented on a display 994 includes a real-time map 954 showing the progress of the delivery person 910 relative to a third smart delivery container system ("third container") 926 that has been positioned along a side 924 of the house 946, with a depiction of the house and container included in the map. In this case, third container 926 is similar to first container 706 of FIG. 7, with UWB device 994 embedded in its housing. In addition, the app 950 offers step-by-step directions 956 ("Go to left side of house") to guide the delivery person 910 to the target micro-destination associated (linked) with the package 900.

As the delivery person 910 approaches the third container 926, the mobile computing device 940 emits a verification or signature signal 942 that, when received by UWB device 994 embedded in the third container 926 causes the container doors 996 to automatically open in anticipation of the package delivery. Once the third container 926 has been opened, the delivery person 910 can deposit the package 900 into the third container 926. The third container 926 can then close its doors 996, and a sanitization cycle performed.

Figure 10:
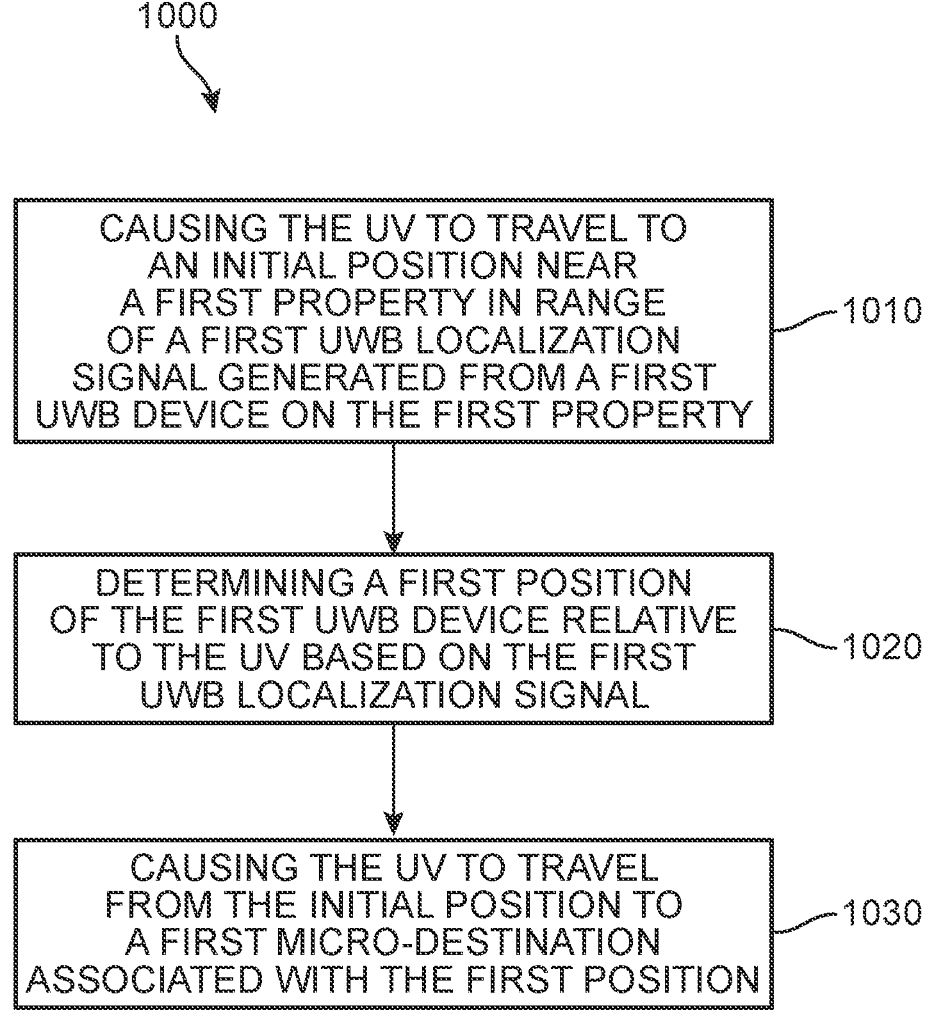
FIG. 10 a flow chart depicting a process of high-precision delivery of items using ultra-wide band (UWB), according to an embodiment.

FIG. 10 is a flow chart illustrating an embodiment of a method 1000 for high-precision delivery of items using ultra-wide band (UWB), such as guiding an unmanned aerial vehicle (UAV) to a micro-destination. A first step 1110 includes causing, via an onboard computing system of an unmanned vehicle (UV), the UV to travel to an initial position near a first property, the initial position being in range of a first UWB localization signal generated from a first UWB device on the first property. A second step 1020 includes determining, at the onboard computing system, a first position of the first UWB device relative to the UV based on the first UWB localization signal. In addition, a third step 1030 includes causing, via the onboard computing system, the UV to travel from the initial position to a first micro-destination associated with the relative first position.

In different embodiments, the method 1000 may include additional steps or aspects. In one embodiment, the method 1000 also includes steps of receiving, at the onboard computing system, a second UWB localization signal generated from the first UWB device, determining, at the onboard computing system and based on the second UWB localization signal, the UV is in a second position relative to the first UWB device ("relative position"), and causing, by the onboard computing system and in response to the UV being in the second position, a package carried by the UV to be released at the first micro-destination. In some embodiments, the method 1000 also includes steps of transmitting, from the onboard computing system and to a smart container in which the first UWB device is embedded, a request signal including an access signature, thereby causing a door of the smart container to open, determining, at the onboard computing system, that an interior chamber of the smart container is directly below the UV, and causing, by the onboard computing system and in response to the interior chamber being directly below the UV, a package carried by the UV to be released for deposit into the interior chamber.

In different embodiments, the method 1000 can also include steps of receiving at a first time, via a delivery management application and at a delivery computing system, a first registration for the first UWB device, adding, at the delivery computing system, the first UWB device to a UWB inventory for a first account, receiving at the delivery computing system, at a second time subsequent to the first time, an order by the first account for delivery of an item, and automatically linking, at the delivery computing system, the delivery of the item to the first UWB device. In another example, the method 1000 also includes steps of receiving, via the delivery management application and at the delivery computing system, a second registration for a second UWB device, and updating, at the delivery computing system, an inventory of UWB devices associated with the first account to include the second UWB device. Furthermore, the method 1000 can in some embodiments include a step of receiving, via the delivery management application and at the delivery computing system, a selection of the first UWB device, where the automatic linking of the delivery of the item to the first UWB device is in response to the selection of the first UWB device. In some embodiments, the method 1000 also includes steps of receiving, at a UWB navigation device (such as a UAV), a UWB signal comprising a unique identifier, scanning an area for a UWB signal comprising the unique identifier, and determining a location of the UWB navigation device based on the UWB signal strength. In another embodiment, a system for providing an LBS using a UWB signal is disclosed, the system including a UWB transmitter configured to transmit a UWB signal comprising a unique identifier, and a UWB navigation device configured to receive the UWB signal, scan an area for the UWB signal, and determine a location of the UWB navigation device based on the UWB signal strength.

Other methods may be contemplated within the scope of the present disclosure. For example, in some embodiments, a method for secure delivery of items using a smart container system is disclosed. The method includes a first step of transmitting, from a first ultra-wide band (UWB) device included in a first smart container disposed at a first property, a first UWB localization signal to a first delivery computing device, and a second step of receiving, at an onboard computing device of the first smart container and from the first delivery computing device, a first request signal. The method also includes a third step of verifying, at the first smart container, that the first request signal represents a valid request to access an interior chamber of the first smart container, and a fourth step of opening, at the first smart container and in response to the verification, a first door to provide access to the interior chamber. A fifth step includes receiving, from a position directly above the interior chamber, a package, and a sixth step includes detecting, via one or more sensors included in a base of the first smart container, a presence of the package. In addition, a seventh step includes closing, in response to detecting the presence of the package, the first door, thereby resealing the first smart container.

In other embodiments, this method may include additional steps or aspects. For example, in one embodiment, the first delivery computing device is carried by a delivery person, and the first UWB localization signal is used by the first delivery computing device to generate a map depicting the first property showing a route superimposed on the map from a current location of the delivery person to a micro-destination associated with the first UWB device. In another embodiment, the first delivery computing device is carried by a delivery person, and the first UWB localization signal is used by the first delivery computing device to generate text-based (step-by-step) navigation directions from a current location of the delivery person to a micro-destination associated with the first UWB device.

In some embodiments, the first delivery computing device is installed on an unmanned vehicle (UV), and the first UWB localization signal is used by the first delivery computing device to guide the UV from its current location to a micro-destination associated with the first UWB device. In one embodiment, the method also includes automatically performing a sanitization cycle within the interior chamber after the first smart container is resealed. In such cases, the sanitization cycle can cause or be implemented by one or both of a UV light and a disinfectant spray that are applied to the package. In another example, the method can include steps of detecting, via a leak sensor embedded in the base, a moisture content level that exceeds a preset threshold, and transmitting, from the onboard computing system, an alert to a mobile computing device associated with an owner of the first smart container (in response to the onboard computing device determining the preset moisture content level threshold was exceeded). In some examples, the first delivery computing device is installed on an unmanned vehicle (UV), and the first UWB localization signal is only received by the first delivery computing device after the UV arrives at a macro-destination represented by the first property.

In other examples, methods disclosed herein can include further steps of transmitting, from the UWB device and to the UV, a handshake signal, and establishing a connection between the UWB device and the UV following the handshake signal. In one embodiment, the method also includes a step of detecting, at the UWB device, one or more external signals indicating the presence of the UV near the UWB device before transmitting the handshake signal. It should be understood that references to a UWB device can include a UWB transmitter, as well as a UWB receiver, and components comprising a computing system as described herein. In different embodiments, the methods can include a step of receiving, at the onboard computing system and from the UWB device, a request for identification prior to receiving the first navigation signal, and transmitting, from the onboard computing device and to the UWB device, identification data for the UV. In another example, the methods can further include steps of receiving, at the UWB device, the identification data, determining, at the UWB device and with reference to a scheduled deliveries knowledge repository (part of the delivery management service), that the identification data corresponds to a UV scheduled to perform a delivery to the property, and generating the first UWB localization signal in response to determining the UV is scheduled to perform a delivery.

In some embodiments, the UWB device is an IoT device mounted on an external surface of a building situated on the property. In one example, the UWB device is a smart doorbell. Light, RF, or other types of signals generated applying one or more of the techniques disclosed herein may be produced by a light emitter, radio emitter or other output device. In some embodiments, the output device may be coupled directly to the system or processor generating the signal. In other embodiments, the output device may be coupled indirectly to the system or processor such as via a network. Examples of such networks include the Internet, mobile telecommunications networks, a WIFI network, as well as any other wired and/or wireless networking system. When the output device is indirectly coupled, the signal generated by the system or processor may be recorded over the network to the server or other computing device. Such records allow applications and other software which track, monitor, or otherwise manage drone deliveries to receive pertinent data.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, smart watches, smart glasses, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

While various embodiments are described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted.

This disclosure includes and contemplates combinations with features and elements known to the average artisan in the art. The embodiments, features, and elements that have been disclosed may also be combined with any conventional features or elements to form a distinct invention as defined by the claims. Any feature or element of any embodiment may also be combined with features or elements from other inventions to form another distinct invention as defined by the claims. Therefore, it will be understood that any of the features shown and/or discussed in the present disclosure may be implemented singularly or in any suitable combination. Accordingly, the embodiments are not to be restricted except in light of the attached claims and their equivalents. Also, various modifications and changes may be made within the scope of the attached claims.

We claim:

1. A method for high-precision delivery of items using ultra-wide band (UWB), the method comprising:

receiving an order from a user for delivery of an item to a first property, the order including a selection by the user of a first micro-destination associated with a first UWB device on the first property out of a plurality of micro-destinations on the first property each associated with a different UWB device out of a plurality of UWB devices;

causing, via an onboard computing system of an unmanned vehicle (UV), the UV to travel to an initial position near the first property, the initial position being in range of one or more of the plurality of UWB devices and in range of a first UWB localization signal generated from the first UWB device on the first property;

determining, at the onboard computing system, a first position of the first UWB device relative to the UV based on the first UWB localization signal; and causing, via the onboard computing system, the UV to travel from the initial position to the first micro-destination associated with the first position of the first UWB device.

2. The method of claim 1, further comprising:

receiving, at the onboard computing system, a second UWB localization signal generated from the first UWB device;

determining, at the onboard computing system and based on the second UWB localization signal, the UV is in a second position relative to the first UWB device; and causing, by the onboard computing system and in response to the UV being in the second position, a package carried by the UV to be released at the first micro-destination.

3. The method of claim 1, further comprising:

transmitting, from the onboard computing system and to a smart container in which the first UWB device is embedded, a request signal including an access signature, thereby causing a door of the smart container to open;

determining, at the onboard computing system, that an interior chamber of the smart container is directly below the UV; and causing, by the onboard computing system and in response to the interior chamber being directly below the UV, a package carried by the UV to be released for deposit into the interior chamber.

4. The method of claim 1, further comprising:

receiving at a first time, via a delivery management application and at a delivery computing system, a first registration for the first UWB device;

adding, at the delivery computing system, the first UWB device to a UWB inventory for a first account;

receiving at the delivery computing system, at a second time subsequent to the first time, an order by the first account for delivery of an item; and automatically linking, at the delivery computing system, the delivery of the item to the first UWB device.

5. The method of claim 4, further comprising:

receiving, via the delivery management application and at the delivery computing system, a second registration for a second UWB device; and updating, at the delivery computing system, an inventory of UWB devices associated with the first account to include the second UWB device.

6. The method of claim 5, further comprising receiving, via the delivery management application and at the delivery computing system, a selection of the first UWB device, wherein the automatic linking of the delivery of the item to the first UWB device is in response to the selection of the first UWB device.

7. A method for secure delivery of items using a smart container system, the method comprising:

transmitting, from a first ultra-wide band (UWB) device included in a first smart container disposed at a first property, a first UWB localization signal to a first delivery computing device;

receiving, at an onboard computing device of the first smart container and from the first delivery computing device, a first request signal;

verifying, at the first smart container, that the first request signal represents a valid request to access an interior chamber of the first smart container;

opening, at the first smart container and in response to the verification, a first door to provide access to the interior chamber;

verifying, using one or more cameras on the first delivery computing device, that the first door has completely opened;

receiving, from a position directly above the interior chamber, a package;

detecting, via one or more sensors included in a base of the first smart container, a presence of the package; and closing, in response to detecting the presence of the package, the first door, thereby resealing the first smart container;

wherein the first smart container includes one or more heating and cooling elements, configured to keep the interior chamber of the first smart container within a predetermined temperature range;

wherein the method further comprises detecting, via a leak sensor embedded in the base, a moisture content level that exceeds a preset threshold; and transmitting, from the onboard computing system, an alert to a mobile computing device associated with an owner of the first smart container.

8. The method of claim 7, wherein the first delivery computing device is carried by a delivery person, and the first UWB localization signal is used by the first delivery computing device to generate a map showing a route from a current location of the delivery person to a micro-destination associated with the first UWB device.

9. The method of claim 7, wherein the first delivery computing device is carried by a delivery person, and the first UWB localization signal is used by the first delivery computing device to generate text-based directions from a current location of the delivery person to a micro-destination associated with the first UWB device.

10. The method of claim 7, wherein the first delivery computing device is installed on an unmanned vehicle (UV), and the first UWB localization signal is used by the first delivery computing device to guide the UV from its current location to a micro-destination associated with the first UWB device.

11. The method of claim 7, further comprising automatically performing a sanitization cycle within the interior chamber after the first smart container is resealed.

12. The method of claim 11, wherein the sanitization cycle causes one or both of a UV light and a disinfectant spray to be applied to the package.

13. The method of claim 7, wherein the first delivery computing device is installed on an unmanned vehicle (UV), and the first UWB localization signal is only received by the first delivery computing device after the UV arrives at a macro-destination represented by the first property.

14. A system for high-precision delivery of items using ultra-wide band (UWB), the system comprising a processor and machine-readable media including instructions which, when executed by the processor, cause the processor to:

receive an order from a user for delivery of an item to a first property, the order including a selection by the user of a first micro-destination associated with a first UWB device on the first property out of a plurality of micro-destinations on the first property each associated with a different UWB device out of a plurality of UWB devices;

cause, via an onboard computing system of an unmanned vehicle (UV), the UV to travel to an initial position near the first property, the initial position being in range of one or more of the plurality of UWB devices and in range of a first UWB localization signal generated from the first UWB device on the first property;

determine, at the onboard computing system, a first position of the first UWB device relative to the UV based on the first UWB localization signal; and cause, via the onboard computing system, the UV to travel from the initial position to the first micro-destination associated with the first position of the first UWB device.

15. The system of claim 14, wherein the instructions further cause the processor to:

receive, at the onboard computing system, a second UWB localization signal generated from the first UWB device;

determine, at the onboard computing system and based on the second UWB localization signal, the UV is in a second position relative to the first UWB device; and cause, by the onboard computing system and in response to the UV being in the second position, a package carried by the UV to be released at the first micro-destination.

16. The system of claim 14, wherein the instructions further cause the processor to:

transmit, from the onboard computing system and to a smart container in which the first UWB device is embedded, a request signal including an access signature, thereby causing a door of the smart container to open;

determine, at the onboard computing system, that an interior chamber of the smart container is directly below the UV; and cause, by the onboard computing system and in response to the interior chamber being directly below the UV, a package carried by the UV to be released for deposit into the interior chamber.

17. The system of claim 14, wherein the instructions further cause the processor to:

receive at a first time, via a delivery management application and at a delivery computing system, a first registration for the first UWB device;

add, at the delivery computing system, the first UWB device to a UWB inventory for a first account;

receive at the delivery computing system, at a second time subsequent to the first time, an order by the first account for delivery of an item; and automatically link, at the delivery computing system, the delivery of the item to the first UWB device.

18. The system of claim 17, wherein the instructions further cause the processor to:

receive, via the delivery management application and at the delivery computing system, a second registration for a second UWB device; and update, at the delivery computing system, an inventory of UWB devices associated with the first account to include the second UWB device.

19. The system of claim 18, wherein the instructions further cause the processor to receive, via the delivery management application and at the delivery computing system, a selection of the first UWB device, wherein the automatic linking of the delivery of the item to the first UWB device is in response to the selection of the first UWB device.

* * * * *